(12) United States Patent
Gunderson et al.

(10) Patent No.: US 7,967,829 B2
(45) Date of Patent: Jun. 28, 2011

(54) MEDICAL DEVICE DELIVERY SYSTEM

(75) Inventors: Richard C. Gunderson, Maple Grove, MN (US); Andrzej M. Malewicz, Minneapolis, MN (US); John R. Moberg, Elk River, MN (US); Gary Pederson, Jr., Albertville, MN (US); Brett Johnson, Roseville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1103 days.

(21) Appl. No.: 10/874,336

(22) Filed: Jun. 23, 2004

(65) Prior Publication Data

US 2005/0080476 A1    Apr. 14, 2005

Related U.S. Application Data

(60) Provisional application No. 60/510,258, filed on Oct. 9, 2003.

(51) Int. Cl.
*A61F 2/84* (2006.01)
(52) U.S. Cl. .............................. 606/108; 623/1.11
(58) Field of Classification Search ................. 606/108; 623/1.11, 1.12, 1.23; 248/125.2
See application file for complete search history.

(56) References Cited

U.S. PATENT DOCUMENTS

| 3,070,057 | A | 7/1959 | Dezzani |
| 4,655,771 | A | 4/1987 | Wallsten |
| 4,665,918 | A | 5/1987 | Garza et al. |
| 4,768,507 | A | 9/1988 | Fischell et al. |
| 4,990,151 | A | 2/1991 | Wallsten |
| 5,026,377 | A | 6/1991 | Burton et al. |
| 5,054,462 | A * | 10/1991 | Larson ............... 124/25.6 |
| 5,160,341 | A | 11/1992 | Brenneman et al. |
| 5,391,172 | A | 2/1995 | Williams et al. |
| 5,433,723 | A | 7/1995 | Lindenberg et al. |
| 5,443,477 | A | 8/1995 | Marin et al. |
| 5,458,615 | A | 10/1995 | Klemm et al. |
| 5,480,423 | A | 1/1996 | Ravenscroft et al. |
| 5,507,768 | A | 4/1996 | Lau et al. |
| 5,534,007 | A | 7/1996 | St. Germain et al. |
| 5,591,172 | A | 1/1997 | Bachmann et al. |
| 5,643,339 | A | 7/1997 | Kavteladze et al. |
| 5,702,418 | A | 12/1997 | Ravenscroft |
| 5,707,376 | A * | 1/1998 | Kavteladze et al. ......... 623/1.11 |
| 5,776,142 | A | 7/1998 | Gunderson |
| 5,782,855 | A | 7/1998 | Lau et al. |
| 5,833,694 | A | 11/1998 | Poncet |
| 5,868,755 | A | 2/1999 | Kanner et al. |
| 5,891,154 | A | 4/1999 | Loeffler |
| 5,906,619 | A | 5/1999 | Olson et al. |
| 5,944,727 | A | 8/1999 | Ahari et al. |
| 5,968,052 | A | 10/1999 | Sullivan, III et al. |
| 6,004,328 | A | 12/1999 | Solar |
| 6,113,607 | A | 9/2000 | Lau et al. |
| 6,143,021 | A | 11/2000 | Staehle |
| 6,146,415 | A | 11/2000 | Fitz |

(Continued)

FOREIGN PATENT DOCUMENTS

EP    0518838    10/1995

(Continued)

*Primary Examiner* — Ryan J Severson
(74) *Attorney, Agent, or Firm* — Seager, Tufte & Wickhem, LLC

(57) ABSTRACT

Medical device delivery systems, as well as related methods and components, are disclosed.

12 Claims, 16 Drawing Sheets

U.S. PATENT DOCUMENTS

| | | | |
|---|---|---|---|
| 6,159,239 | A | 12/2000 | Greenhalgh |
| 6,162,231 | A | 12/2000 | Mikus et al. |
| 6,190,360 | B1 | 2/2001 | Iancea et al. |
| 6,193,194 | B1 | 2/2001 | Minovitch |
| 6,203,550 | B1 | 3/2001 | Olson |
| 6,221,081 | B1 | 4/2001 | Mikus et al. |
| 6,238,402 | B1 | 5/2001 | Sullivan, III et al. |
| 6,238,430 | B1 | 5/2001 | Klumb et al. |
| 6,248,122 | B1 | 6/2001 | Klumb et al. |
| 6,254,633 | B1 | 7/2001 | Pinchuk et al. |
| 6,336,938 | B1 | 1/2002 | Kavteladze et al. |
| 6,338,739 | B1 | 1/2002 | Datta et al. |
| 6,383,211 | B1 | 5/2002 | Staehle |
| 6,383,216 | B1 | 5/2002 | Kavteladze et al. |
| 6,391,051 | B2 | 5/2002 | Sullivan, III et al. |
| 6,395,017 | B1 | 5/2002 | Dwyer et al. |
| 6,402,760 | B1 | 6/2002 | Fedida |
| 6,488,694 | B1 | 12/2002 | Lau et al. |
| 6,488,700 | B2 | 12/2002 | Klumb et al. |
| 6,514,261 | B1 | 2/2003 | Randall et al. |
| 6,517,558 | B2 | 2/2003 | Gittings et al. |
| 6,517,569 | B2 | 2/2003 | Mikus et al. |
| 6,520,983 | B1 | 2/2003 | Colgan et al. |
| 6,527,779 | B1 | 3/2003 | Rourke |
| 6,527,789 | B1 | 3/2003 | Lau et al. |
| 6,572,643 | B1 | 6/2003 | Gharibadeh |
| 6,582,459 | B1 | 6/2003 | Lau et al. |
| 6,589,251 | B2 | 7/2003 | Yee et al. |
| 6,599,296 | B1 | 7/2003 | Gillick et al. |
| 6,602,280 | B2 | 8/2003 | Chobotov |
| 6,660,031 | B2 | 12/2003 | Tran et al. |
| 6,663,666 | B1 | 12/2003 | Quiachon et al. |
| 6,866,669 | B2 | 3/2005 | Buzzard et al. |
| 6,939,352 | B2 | 9/2005 | Buzzard et al. |
| 2001/0004699 | A1 | 6/2001 | Gittings et al. |
| 2001/0025643 | A1 | 10/2001 | Foley |
| 2001/0028323 | A1 | 10/2001 | Walley et al. |
| 2001/0037141 | A1 | 11/2001 | Yee et al. |
| 2001/0041902 | A1 | 11/2001 | Lepulu et al. |
| 2002/0004663 | A1 | 1/2002 | Gittings et al. |
| 2002/0062129 | A1 | 5/2002 | Mikus et al. |
| 2002/0077566 | A1 | 6/2002 | Laroya et al. |
| 2002/0095204 | A1 | 7/2002 | Thompson et al. |
| 2002/0111666 | A1 | 8/2002 | Hart et al. |
| 2002/0144696 | A1 | 10/2002 | Sharkawy et al. |
| 2002/0151955 | A1 * | 10/2002 | Tran et al. ............... 623/1.12 |
| 2002/0161424 | A1 | 10/2002 | Rapacki et al. |
| 2002/0182827 | A1 | 12/2002 | Abe et al. |
| 2002/0183827 | A1 | 12/2002 | Derus et al. |
| 2002/0188342 | A1 | 12/2002 | Rykhus, Jr. et al. |
| 2003/0028236 | A1 * | 2/2003 | Gillick et al. ............. 623/1.11 |
| 2003/0069629 | A1 | 4/2003 | Jadhav et al. |
| 2003/0074045 | A1 | 4/2003 | Buzzard et al. |
| 2003/0144671 | A1 | 7/2003 | Brooks et al. |
| 2003/0167060 | A1 | 9/2003 | Buzzard et al. |
| 2004/0006380 | A1 | 1/2004 | Buck et al. |
| 2004/0010265 | A1 | 1/2004 | Karpiel |
| 2004/0093056 | A1 | 5/2004 | Johnson et al. |
| 2004/0148009 | A1 | 7/2004 | Buzzard et al. |
| 2004/0181135 | A1 | 9/2004 | Drysen |
| 2004/0181239 | A1 | 9/2004 | Dorn et al. |
| 2004/0193180 | A1 | 9/2004 | Buzzard et al. |
| 2005/0021123 | A1 | 1/2005 | Dorn et al. |
| 2005/0060016 | A1 | 3/2005 | Wu et al. |
| 2005/0182475 | A1 | 8/2005 | Jen et al. |
| 2006/0074477 | A1 | 4/2006 | Berthiaume et al. |

FOREIGN PATENT DOCUMENTS

| | | |
|---|---|---|
| EP | 1 302 178 | 4/2003 |
| EP | 0957824 | 8/2003 |
| EP | 1383446 | 11/2005 |
| WO | WO 00/02503 | 1/2000 |
| WO | WO 00/18330 | 4/2000 |
| WO | WO 01/56504 | 8/2001 |
| WO | WO 02/066094 | 8/2002 |
| WO | WO 02/087470 | 11/2002 |
| WO | WO 03/010134 | 2/2003 |
| WO | WO 2006/036472 | 4/2006 |

* cited by examiner

MEDICAL DEVICE DELIVERY SYSTEM

RELATED APPLICATIONS

This application claims priority from U.S. Provisional Application No. 60/510,258 filed Oct. 9, 2003, which is hereby incorporated by reference in its entirety.

TECHNICAL FIELD

This invention relates to medical device delivery systems, as well as related methods and components.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include an outer tube surrounding an inner tube with a stent positioned therebetween. Generally, the operator of the system positions the distal portion within the lumen at a desired location (e.g., so that the stent is adjacent an occlusion). The operator can then retract the outer tube to allow the stent to engage the occlusion/lumen wall, and the operator subsequently removes the distal portion of the system from the lumen. In many instances, the handle includes one or more devices that the operator of the system can use to retract the outer tube to allow the stent to engage the occlusion/lumen wall.

SUMMARY

This invention relates to medical device delivery systems, as well as related methods and components.

In one aspect, the invention features a system that includes an inner tube, an outer tube and an actuator. The outer tube at least partially surrounds the inner tube so that a medical device can be positioned between the inner and outer tubes. The inner and outer tubes are configured to be capable of being disposed within a body lumen. The actuator is configured so that, as a force is applied to the actuator, the actuator can cause relative motion between the inner and outer tubes. The mechanical advantage of the actuator can change as the actuator moves.

In another aspect, the invention features a system that includes an inner tube, an outer tube and an actuator. The outer tube at least partially surrounds the inner tube so that a medical device can be positioned between the inner and outer tubes. The inner and outer tubes are configured to be capable of being disposed within a body lumen. The actuator is configured so that, as a force is applied to the actuator, the actuator can cause relative motion between the inner and outer tubes. As the actuator moves, an amount of force applied to the actuator increases for the inner and outer tubes to move a given distance relative to each other.

In a further aspect, the invention features a system that includes an inner tube, an outer tube, a first actuator and a second actuator. The outer tube at least partially surrounds the inner tube so that a medical device can be positioned between the inner and outer tubes. The inner and outer tubes are configured to be capable of being disposed within a body lumen. The first actuator is configured so that, as a force is applied to the first actuator, the inner and outer tubes can move relative to each other. The second actuator is configured so that, as a force is applied to the second actuator, the inner and outer tubes can move relative to each other. The first and second actuators are configured so that they cannot be simultaneously used to move the inner and outer tubes relative to each other.

In one aspect, the invention features a system that includes an inner tube, an outer tube, a first actuator and a second actuator. The outer tube at least partially surrounds the inner tube so that a medical device can be positioned between the inner and outer tubes. The inner and outer tubes are configured to be capable of being disposed within a body lumen. The first actuator is configured so that, as a force is applied to the first actuator, the inner and outer tubes can move relative to each other. The first actuator has a maximum distance that it can move the inner and outer tubes relative to each other. The second actuator is configured so that, as a force is applied to the second actuator, the inner and outer tubes can move relative to each other. The system is configured so that the second actuator cannot be used to move the inner and outer tubes relative to each other until the first actuator has been used to move the inner and outer tubes the maximum distance relative to each other that the first actuator can move the inner and outer tubes relative to each other.

In another aspect, the invention features a system that includes an inner tube, an outer tube and an actuator. The outer tube at least partially surrounds the inner tube so that a medical device can be positioned between the inner and outer tubes. The inner and outer tubes are configured to be capable of being disposed within a body lumen. The actuator is configured so that, as a force is applied to the first actuator, the inner and outer tubes can move relative to each other. The actuator has first and second stages of operation. In the first stage of operation the actuator is capable of moving the inner and outer tubes relative to each other as the actuator is rotated, and in the second stage of operation the actuator being capable of moving the inner and outer tubes relative to each other as the actuator is moved linearly.

Embodiments can include one or more of the following features.

The mechanical advantage of an actuator can change as the actuator rotates about an axis that is collinear with the outer tube.

The mechanical advantage of an actuator can change as the actuator rotates about an axis that is perpendicular to the outer tube.

The mechanical advantage of an actuator can change continuously as the actuator moves.

The mechanical advantage of an actuator can decrease as the actuator moves.

An actuator can be formed of a rotatable member (e.g., a cam) having a radius that increases as the actuator rotates. The system can further include a windable member that couples the rotatable member to the outer tube. The windable member can be, for example, a wire, a cord, a ribbon or a flat gears.

An actuator can be formed of a rotatable member and a shaft, with the shaft being coupled to the rotatable member and configured so that, as the rotatable member rotates, the outer tube moves. As examples, the rotatable member can have a groove and the shaft can have a projecting member that mates with the groove, or the shaft can have a groove and the rotatable member can have a projecting member that mates with the groove. The pitch of the groove can vary (e.g., vary continuously).

The system can further include a housing coupled to the actuator. An actuator can be at least partially disposed within the housing. At least a portion of the housing can be proximal to a proximal end of the outer tube. The housing can be configured to be held by an operator of the system during use of the system.

As a force is applied to the actuator, the actuator can cause the outer tube to move.

An actuator can be coupled to the outer tube, the inner tube or both.

Embodiments of the invention can provide one or more of the following advantages.

In some embodiments, the systems can provide relatively fine and/or controlled movement of the outer tube as the outer tube is retracted. By fine and/or controlled movement, it is generally meant that an operator of the system can use the system to achieve refined and/or small scale movement of outer tube in a relatively controlled fashion as the outer tube is retracted. For example, the systems can provide relatively fine and/or controlled movement of the outer tube as the outer tube is initially retracted to expose the medical device. The relatively fine and/or controlled movement of the outer tube can be maintained during the entire process of retracting the outer tube, or the relatively fine and/or controlled movement of the outer tube can be maintained for only a portion of the outer tube retraction process (e.g., until at least a portion of the medical device is exposed and/or engages the lumen wall). The relatively fine and/or controlled movement of the outer tube can enhance the accuracy of placement of the medical device (e.g., in a body lumen).

In certain embodiments, the systems can include one or more actuators to provide variable (e.g., continuously variable) mechanical advantage as the actuator(s) is/are moved (e.g., linearly moved, rotationally moved) to retract the outer tube and expose the medical device (e.g., for placement in a body lumen). For example, the mechanical advantage can decrease as the actuator(s) is/are moved. This can allow for varying degrees of fineness/coarseness in the movement of the outer tube as the actuator(s) is/are moved. For example, the actuator(s) can be designed to provide a relatively high mechanical advantage as the outer tube is retracted to initially expose the medical device, and a relatively low mechanical advantage as the outer tube is further retracted. This can, for example, allow for relatively fine and/or controlled movement of the outer tube as the medical device is initially exposed, and subsequent relatively coarse movement of the outer tube (e.g., as the remaining portion of the medical device is exposed after the medical device initially engages the lumen wall, after the medical device is fully exposed and engaged with the lumen wall).

In some embodiments, a single actuator is used to provide variable (e.g., continuously variable) mechanical advantage. This feature can be desirable because it can allow the operator of the system to use single hand/thumb/finger to retract the outer tube (e.g., for both relatively fine and/or controlled movement of the outer tube and for relatively coarse movement of the outer tube).

In certain embodiments, the systems include a single actuator for which the amount of force applied to the actuator to make the outer tube move a given distance varies (e.g., continuously varies) as the actuator is moved. For example, the amount of force applied to the actuator to make the outer tube move a given distance can decrease as the actuator is moved. This can, for example, allow the actuator to provide both relatively fine and/or controlled movement of the outer tube (e.g., as the medical device is initially exposed) and for relatively coarse movement of the outer tube (e.g., as the remaining portion of the medical device is exposed after the medical device initially engages the lumen wall, after the medical device is fully exposed and engaged with the lumen wall).

In some embodiments, the systems use one actuator to move the outer tube, where the actuator has one stage in which rotational movement of the actuator is used to retract the outer tube (e.g., to achieve relatively fine and/or controlled movement of the outer tube) and a second stage in which linear movement of the actuator is used to move the outer tube (e.g., to achieve relatively coarse movement of the outer tube).

In certain embodiments, the systems use two actuators to retract the outer tube, with the system being designed so that both actuators cannot be used simultaneously. For example, one actuator can be used to achieve relatively fine movement of the outer tube (e.g., as the medical device is initially exposed), and a different actuator can be used to achieve relatively coarse movement of the outer tube (as the remaining portion of the medical device is exposed after the medical device initially engages the lumen wall, after the medical device is fully exposed and engaged with the lumen wall).

In some embodiments, the systems use first and second actuators to retract the outer tube, with the system being designed so that second actuator cannot be used until the first actuator has moved the outer tube a maximum distance that the first actuator can move the outer tube. For example, one actuator can be used to achieve relatively fine movement of the outer tube (e.g., as the medical device is initially exposed), and a different actuator can be used to achieve relatively coarse movement of the outer tube (as the remaining portion of the medical device is exposed after the medical device initially engages the lumen wall, after the medical device is fully exposed and engaged with the lumen wall).

Features and advantages of the invention are in the description, drawings and claims.

DETAILED DESCRIPTION

Figure 1:
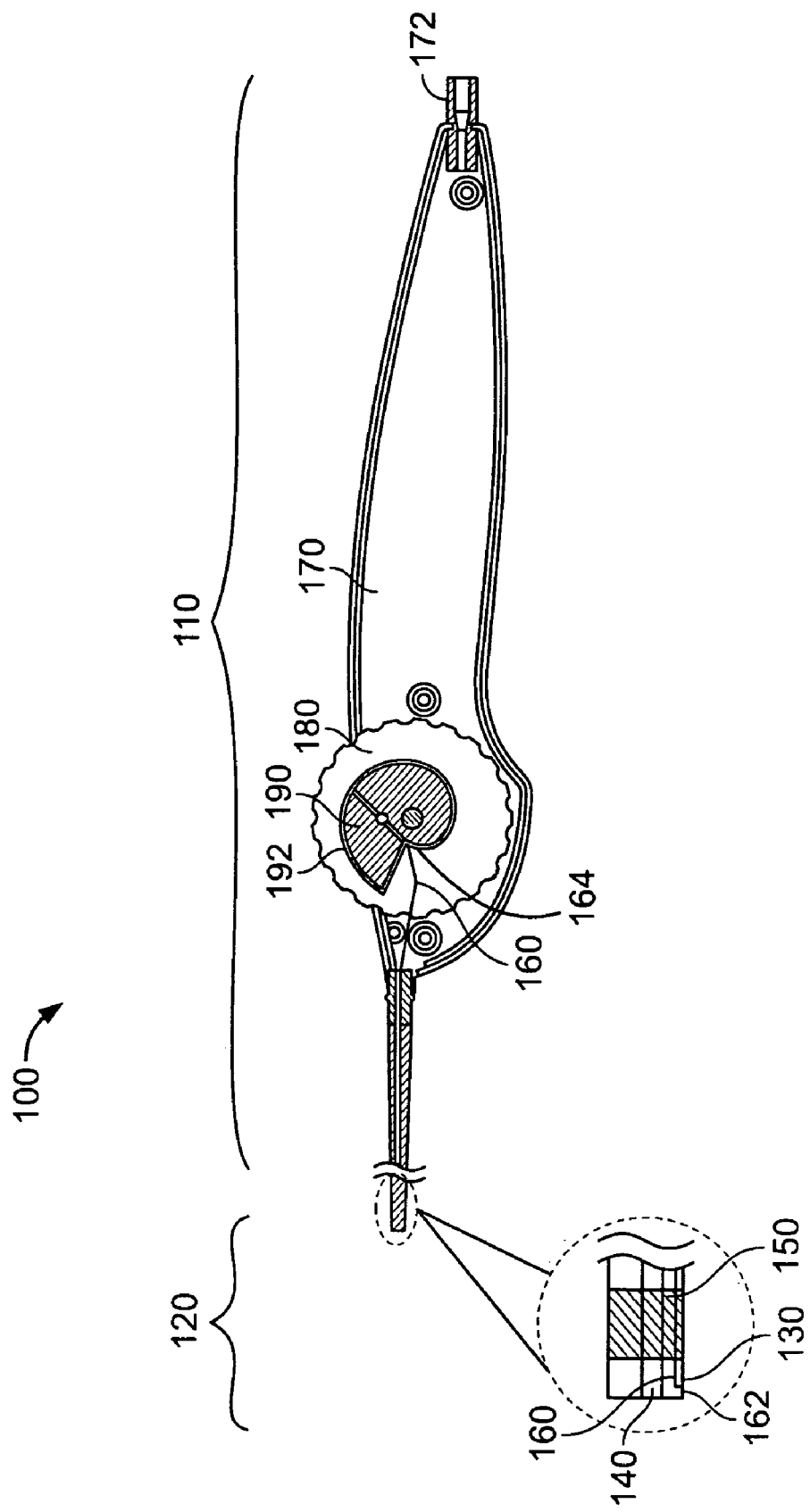
FIG. 1 is a cross-sectional view of an embodiment of a stent delivery system.
Figure 2:
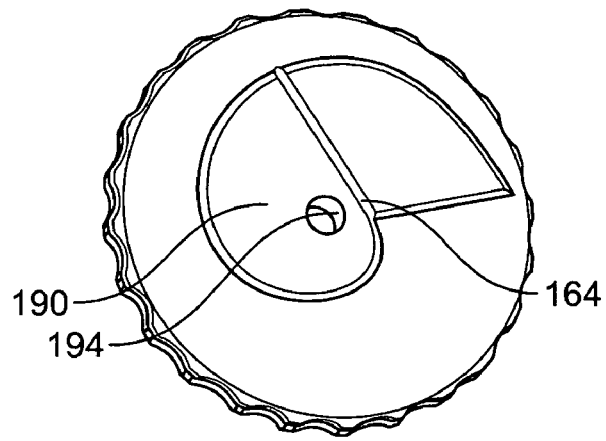
FIG. 2 is a perspective view of the cam and thumb wheel portion of the stent delivery system of FIG. 1.
Figure 3:
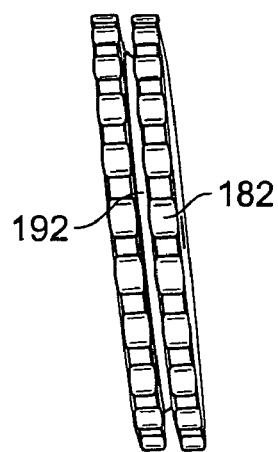
FIG. 3 is a side view of the thumb wheel portion of the stent delivery system of FIG. 1.
Figure 4:
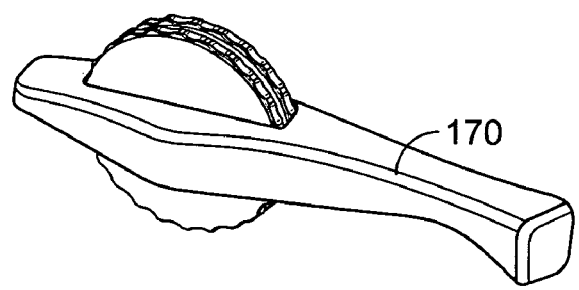
FIG. 4 is a perspective view of the handle and thumb wheel portion of the stent delivery system of FIG. 1.

FIGS. 1-4 show a stent delivery system 100 having a proximal portion 110 and a distal portion 120. System 100 includes an outer tube 130, an inner tube 140 and a stent 150 positioned between outer tube 130 and inner tube 140. Delivery system 100 also includes a wire 160 that is connected to outer tube 130 at a distal location 162 and connected to a cam 190 at a proximal location 164 (e.g., a slit in cam 190 into which wire 160 can fit) so that wire 160 couples outer tube 130 to cam 190. Cam 190 is mounted on a thumb wheel 180 having knurls 182 (FIG. 3). Thumb wheel 180 is partially disposed within a handle 170 having a guide wire port 172.

With this configuration, as thumb wheel 180 is rotated, cam 190 rotates about an axis 194 that is perpendicular to outer tube 130, and wire 160 winds around outer periphery 192 of cam 190. Because outer periphery 192 increases as cam 190 is rotated, the mechanical advantage provided by cam 190 decreases as cam 190 is rotated. This can allow for relatively fine and/or controlled retraction of outer tube 130 as cam 190 is initially rotated (as wire 160 winds around a portion of outer periphery 192 which is relatively large to retract outer tube 130 and initially expose stent 150), and can also allow for relatively coarse movement of outer tube 130 as cam 190 is later rotated (as wire 160 winds around a portion of outer periphery 192 which is relatively small to retract outer tube 130 after stent 150 is initially exposed and at least partially engaged with a body lumen).

In some embodiments, outer periphery 192 is dimensioned to be about the same as or greater than the distance that outer tube 130 travels to fully expose stent 150. In such embodiments, stent 150 is fully exposed by rotating thumb wheel 180 and cam 190 so that wire 160 is wrapped around periphery 192 a single time. In other embodiments, outer periphery 192 can be dimensioned differently.

Figure 5:
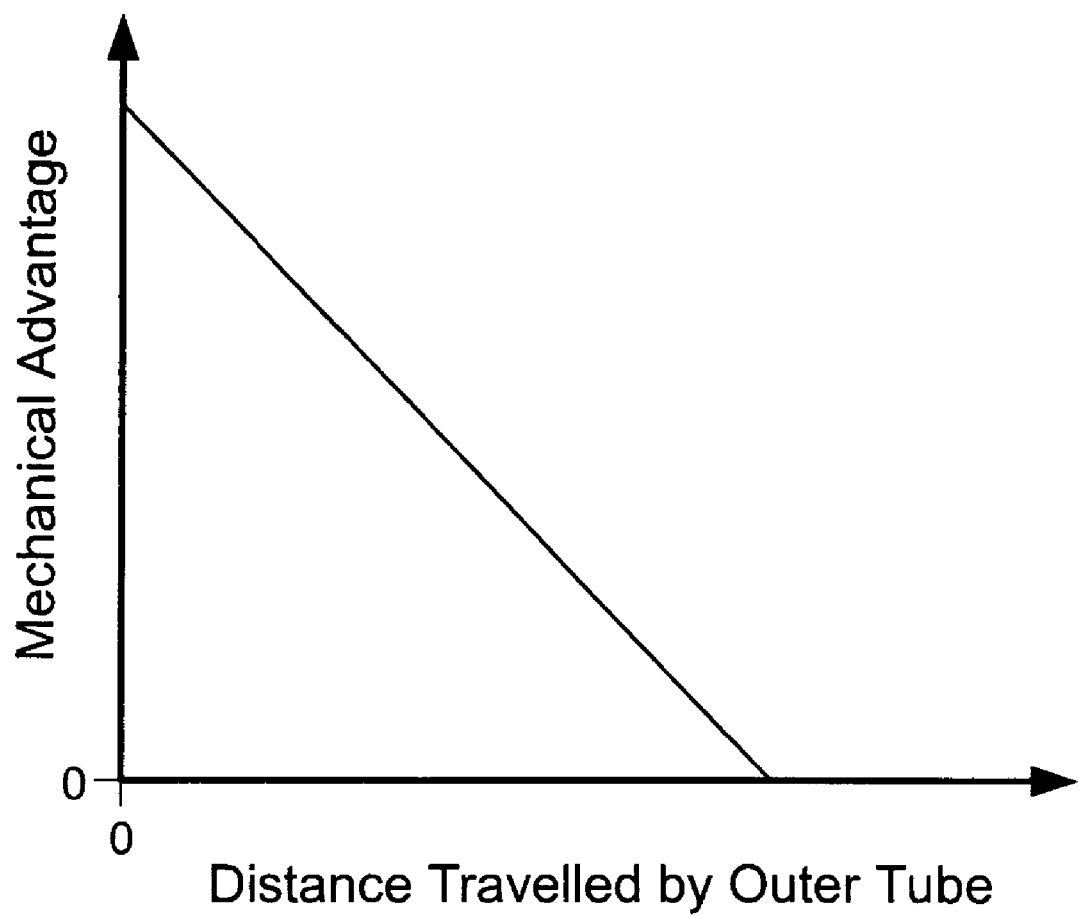
FIG. 5 is a graph showing mechanical advantage as a function of retraction distance of the outer tube.

FIG. 5 depicts a graph which is representative in nature and generally demonstrates the variation in mechanical advantage that can be provided by cam 190 as cam 190 is rotated and outer tube 130 is retracted. As shown in FIG. 5, the variation in the mechanical advantage of cam 190 can be continuous and monotonically decrease as outer tube 130 is retracted. Although depicted in FIG. 5 as varying in a linear fashion, in some embodiments, the mechanical advantage of cam 190 can vary in a non-linear fashion.

Figure 6A:
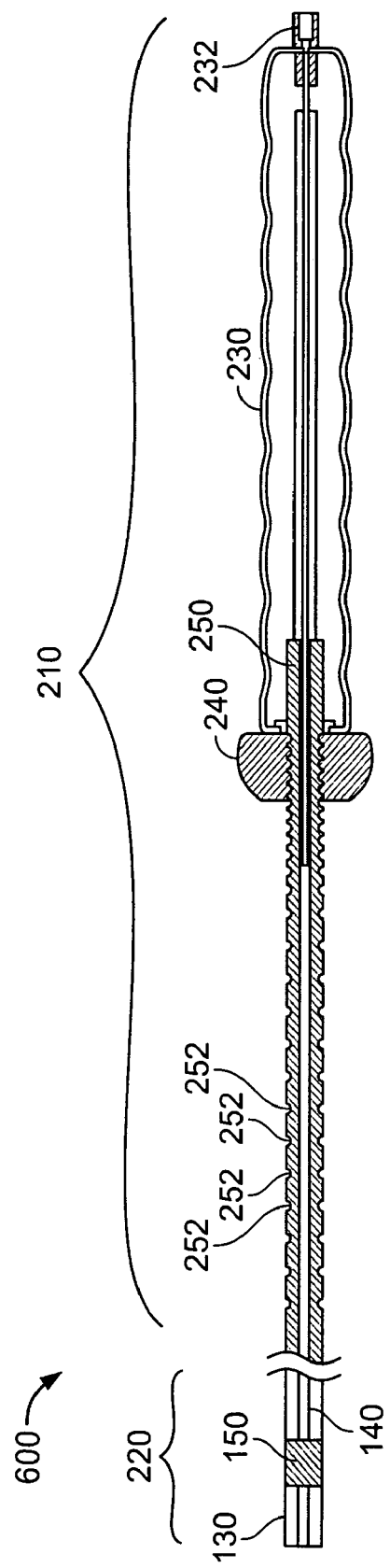
FIG. 6A is a cross-sectional view of an embodiment of a stent delivery system.
Figure 6B:
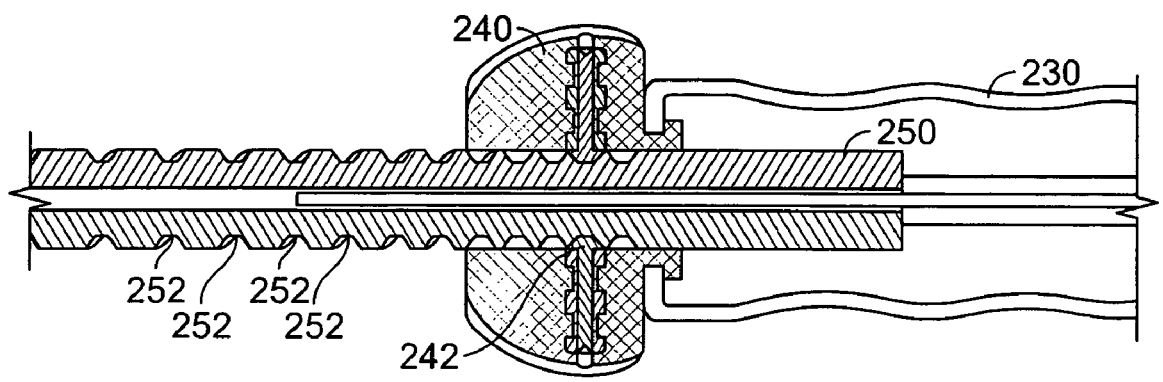
FIG. 6B is a partial cross-sectional view of a portion of the proximal portion of the stent delivery system of FIG. 6A.
Figure 6C:
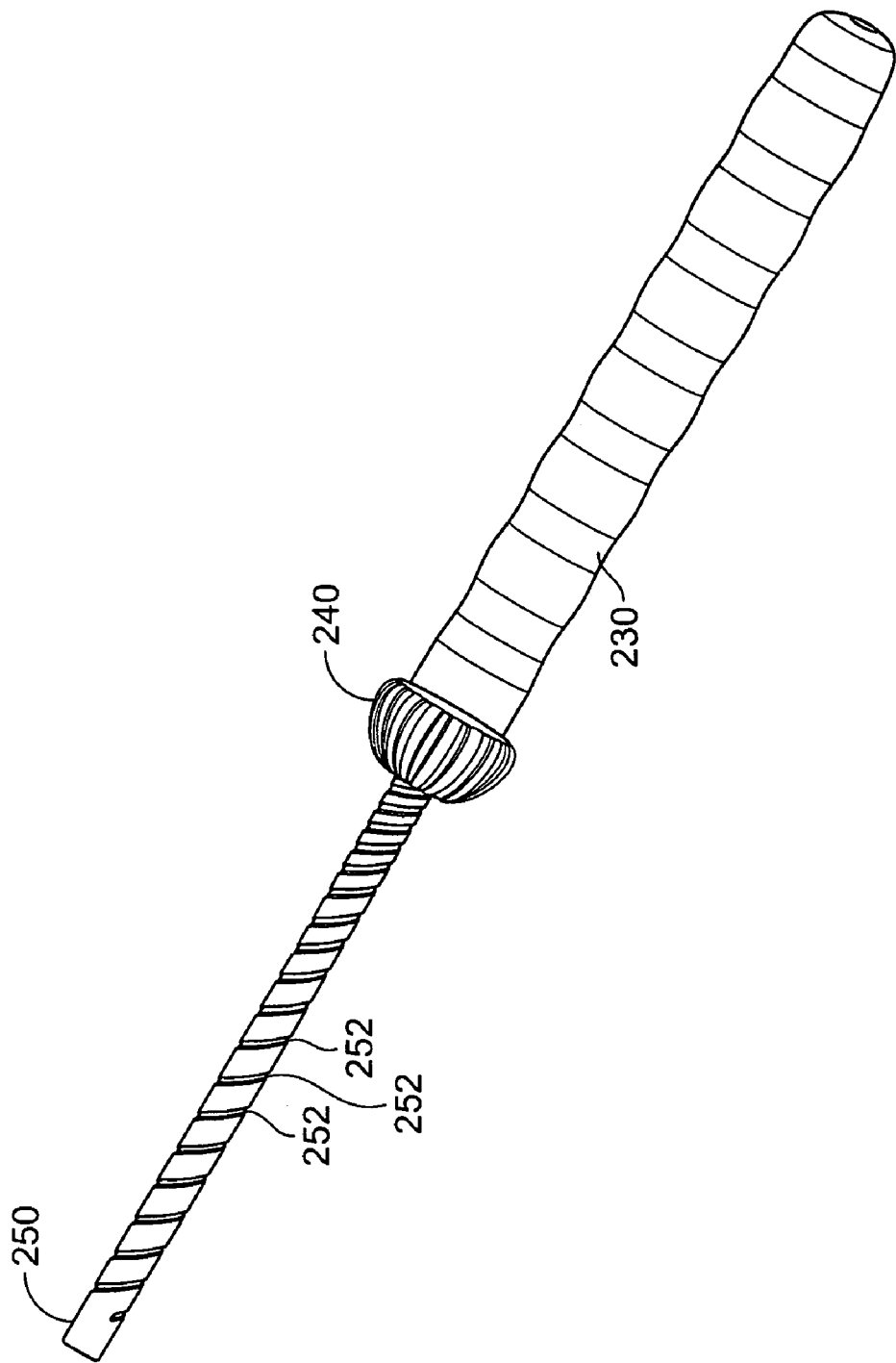
FIG. 6C is a perspective view of the proximal portion of the stent delivery system of FIG. 6A.
Figure 7:
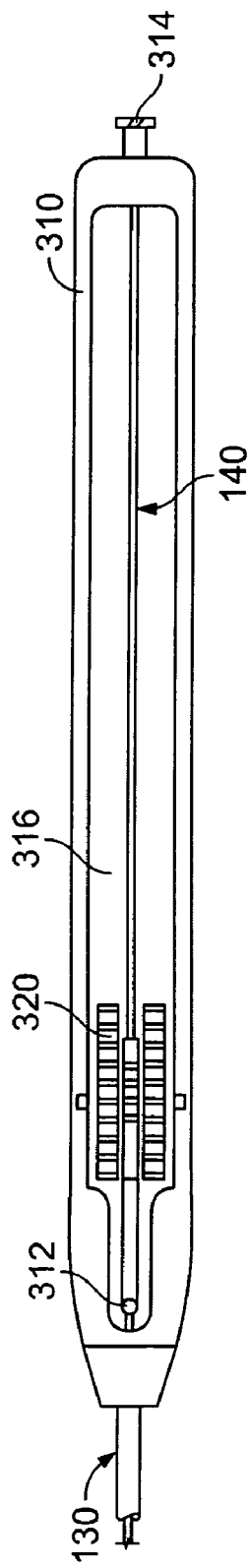
FIGS. 7 and 8 are top and cross-sectional views, respectively, of the proximal portion of an embodiment of a stent delivery system.

FIGS. 6A-6C show a stent delivery system 200 that also uses a single actuator to achieve continuous change in mechanical advantage. System 200 includes a proximal portion 210 and a distal portion 220. System 200 includes a handle 230 that is coupled to a rotatable member 240. Handle 230 houses a shaft 250 having a groove 252 that mates a projecting member (e.g., a tooth, a pin, a dowel) 242 in rotatable member 240 so that, as rotatable member 240 is rotated about an axis collinear with outer tube 130, shaft 250 moves proximally. Shaft 250 is coupled to outer tube 130 so that, as shaft 250 moves proximally, outer tube 130 is retracted. Groove 252 have a continuously variable pitch so that the mechanical advantage of rotatable member 240/shaft 250 varies continuously as rotatable member 240 is rotated and outer tube 130 is retracted.

As shown in FIGS. 6A-6C, the pitch of groove 252 increases as shaft 250 is rotated to retract outer tube 130, resulting in a decrease in mechanical advantage of rotatable member 240/shaft 250 as outer tube 130 retracts. This can allow for relatively fine and/or controlled retraction of outer tube 130 as rotatable member 240 is initially rotated (as projecting member 242 engages groove 252 at a location where groove 252 has a relatively high pitch to retract outer tube 130 and initially expose stent 150), and can also allow for relatively coarse movement of outer tube 130 as rotatable member 240 is later rotated (as projecting member 242 engages groove 252 as a location where groove 252 has a relatively low pitch to retract outer tube 130 after stent 150 is initially exposed and at least partially engaged with a body lumen).

Figure 8:
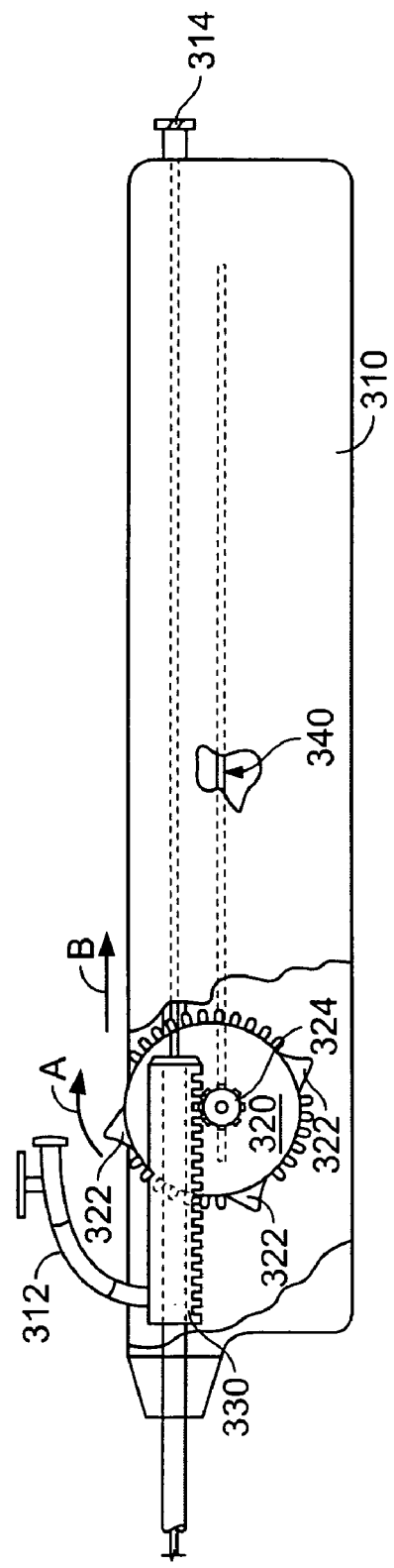
Figure 9:
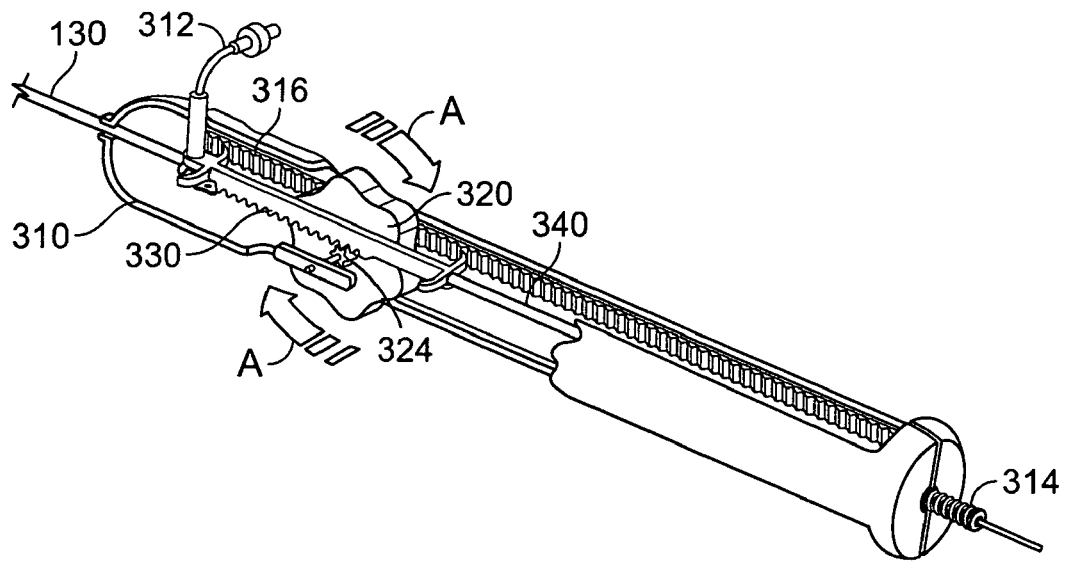
FIG. 9 is a partial cut away view of the proximal portion stent delivery system of FIGS. 7 and 8.

While systems have been shown in which a single actuator is used to achieve continuous change in mechanical advantage, in some embodiments, a single actuator is used to achieve a non-continuous change in mechanical advantage. For example, FIGS. 7-10 show the proximal portion of a stent delivery system 300. System 300 includes a handle 310 with a fluid flush port 312 and a guide wire port 314. Handle 310 is partially housed in a rotatable dial 320 that has finger rests 322. Dial 320 also includes a pinion 324 that is designed to engage a rack 330 so that, while pinion 324 is engaged with rack 330, rotation of dial 320 (arrow A) results in linear movement of dial 320. As depicted in FIG. 8, clockwise rotation of dial 320 while pinion 324 is engaged with rack 330 results in proximal linear movement of dial 320. As dial 320 moves linearly, pinion 324 becomes disengaged from rack 330, at which point dial 320 can move linearly (arrow B) in the proximal direction along track 340 by pulling one of the finger rests 322 of dial 320.

Alternatively, system 300 can include an actuator (e.g., a finger ring) in addition to dial 320 that is coupled to dial 320 and outer tube 130 so that, as pinion 324 becomes disengaged from rack 330, the additional actuator (e.g., finger ring) becomes exposed. For example, the additional actuator can be disposed within the distal portion of opening 316 in handle 310 when pinion 324 is engaged with rack 330 so that the additional actuator is hidden from and/or inaccessible to an operator of system 300 until pinion 324 becomes disengaged from rack 330, at which point the additional actuator becomes accessible to the operator of system 300.

Dial 320 is coupled to outer tube 130 so that dial 320 has two different stages of movement relative to the movement of outer tube 130. In a first stage, pinion 324 is engaged with rack 330, and rotation of dial 320 results in retraction of outer tube 130. In a second stage, pinion 324 is disengaged from rack 330, and linear movement of dial 320 results in retraction of outer tube 130. As shown in FIGS. 7-10, the two stages of movement of dial 320 cannot be used simultaneously, and the second stage of movement of dial 320 cannot be used until the first stage of movement of dial 320 has been used to retract outer tube 130 the maximum distance that the first stage can retract outer tube 130.

Figure 10:
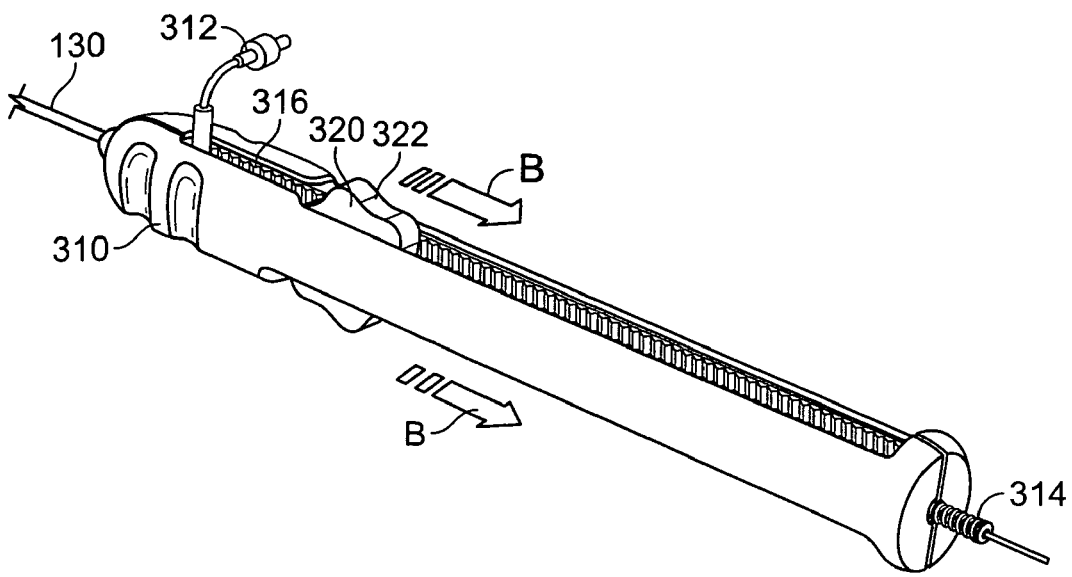
FIG. 10 is a perspective view of the proximal portion stent delivery system of FIGS. 7 and 8.
Figure 11:
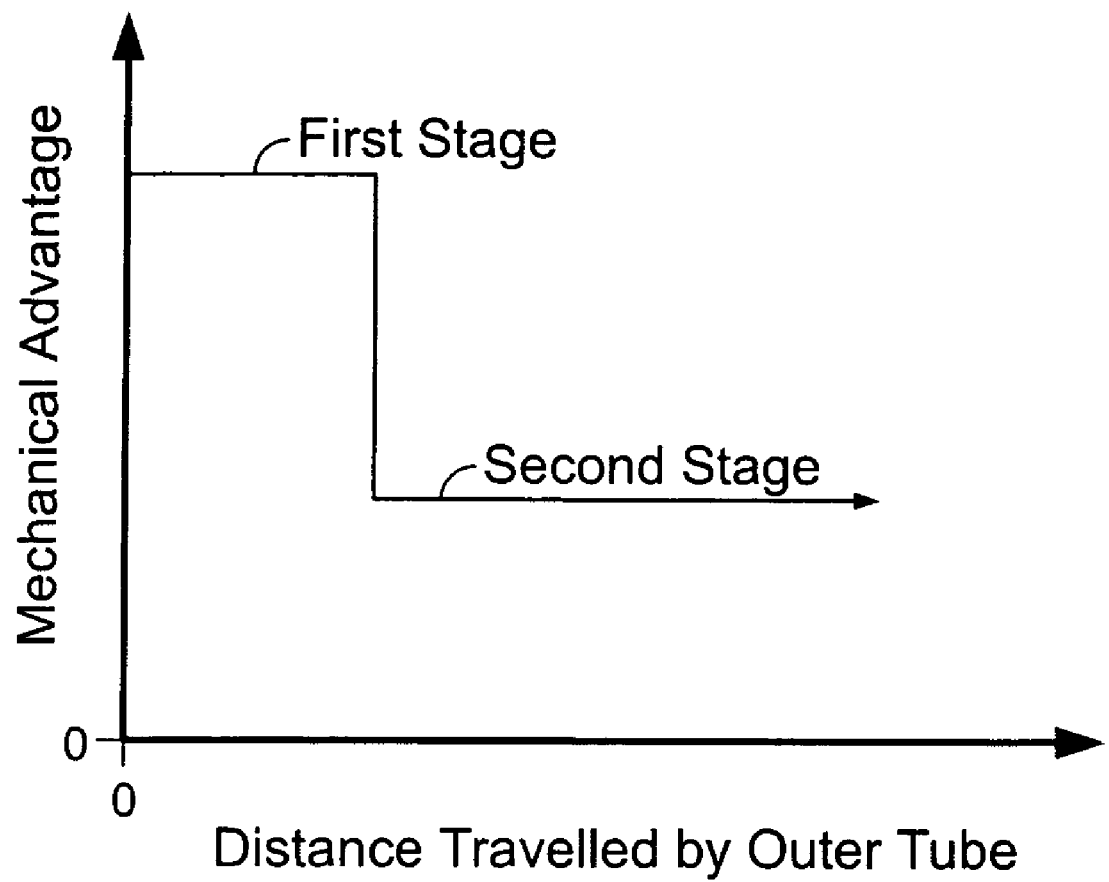
FIG. 11 is a graph showing mechanical advantage as a function of retraction distance of the outer tube.

FIG. 11 depicts a graph which is representative in nature and generally demonstrates the variation in mechanical advantage that can be provided by dial 320 as dial 320 is rotated in a first stage and then moved linearly in a second stage. As shown in FIG. 10, the variation in the mechanical advantage of dial 320 can be in the form of a step function.

Figure 12:
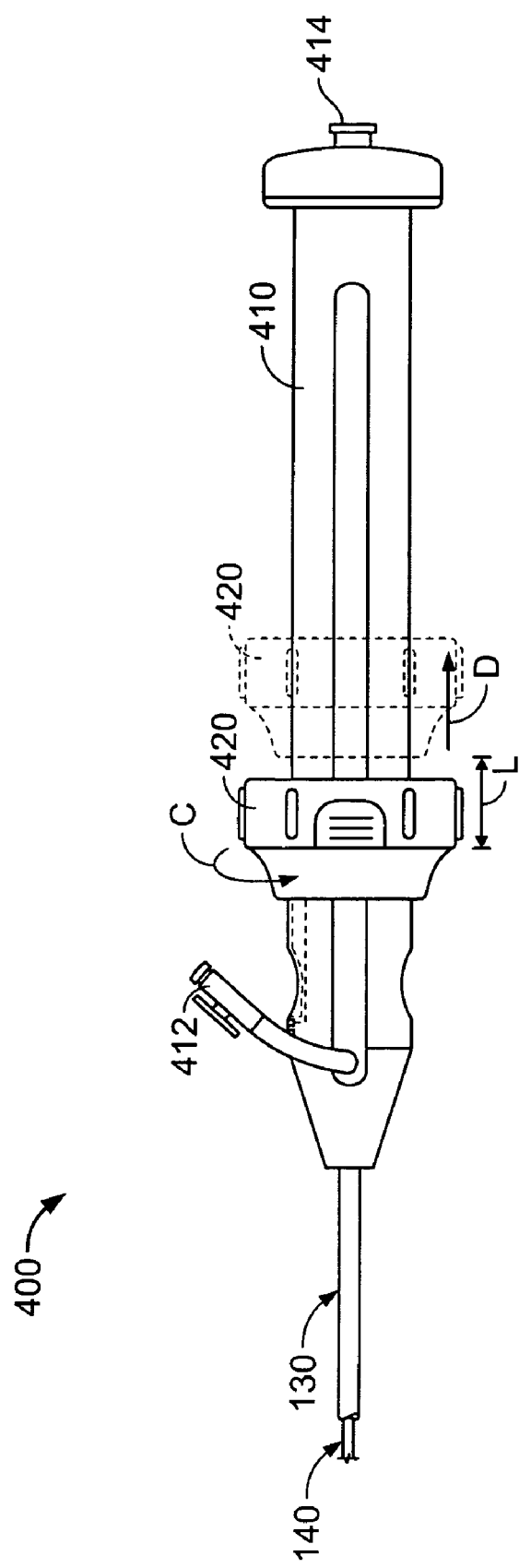
FIG. 12 is a top view of the proximal portion of an embodiment of a stent delivery system.
Figure 13:
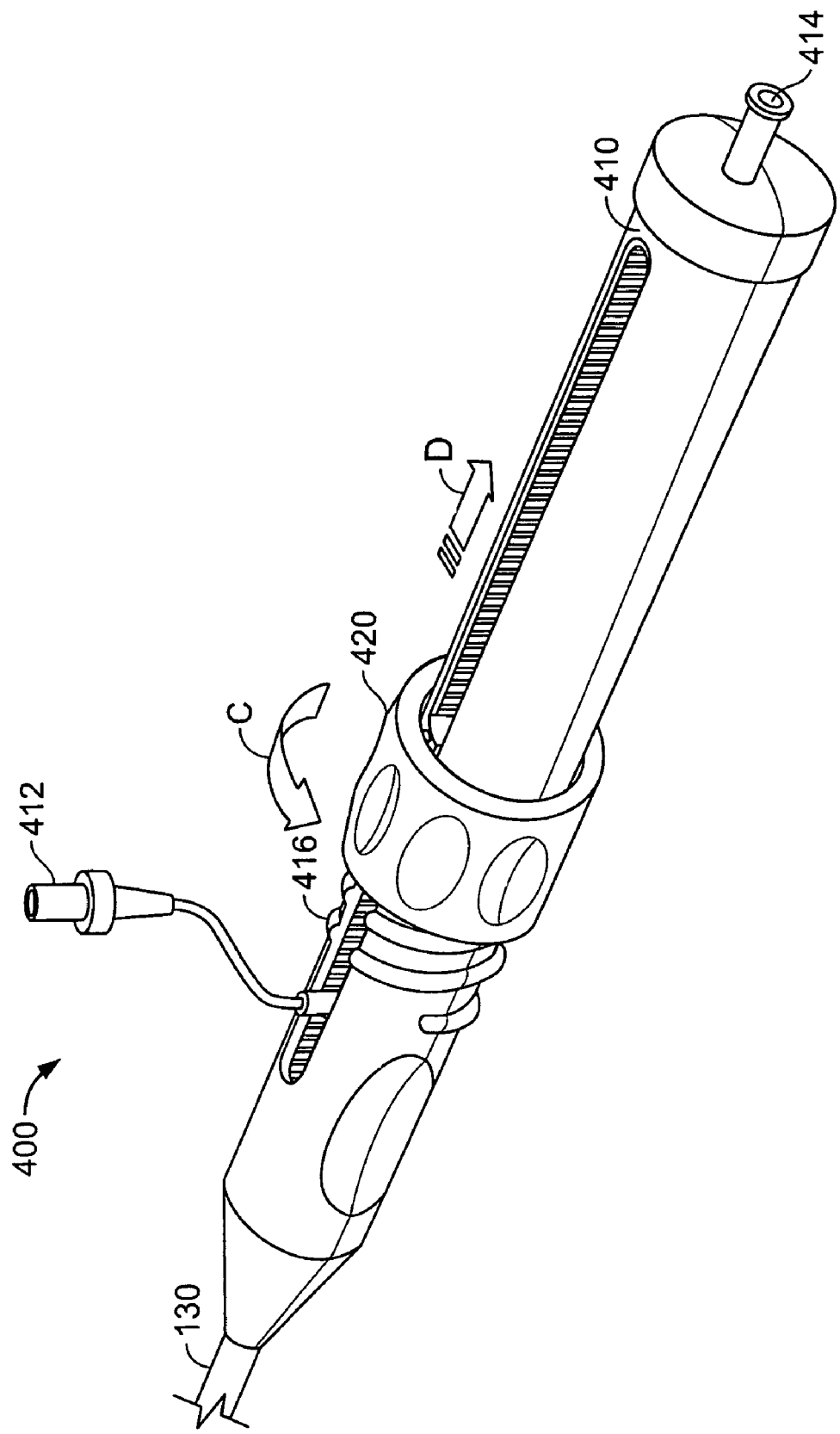
FIG. 13 is a perspective view of the proximal portion of the stent delivery system of FIG. 12.

FIGS. 12 and 13 show the proximal portion of a system 400 having one actuator to achieve non-continuous change in mechanical advantage. System 400 includes a handle 410 with a fluid flush port 412 and a guide wire port 414. A rotatable dial 420 has a groove that mates with thread 416 in the outer surface of handle 410 so that, as dial 420 rotates and engages thread 416, dial 420 moves linearly. As depicted in FIGS. 12 and 13, counterclockwise rotation of dial 420 (Arrow C) results in proximal linear movement of dial 420. As dial 420 moves linearly(distance L in FIG. 12), the groove in dial 420 become disengaged from thread 416, at which point dial 420 can move linearly (arrow D) in the proximal direction by pulling dial 420.

Dial 420 is coupled to outer tube 130 so that dial 420 has two different stages of movement relative to the movement of outer tube 130. In a first stage, groove in dial 420 are engaged with thread 416 in handle 410, and rotation of dial 420 results in retraction of outer tube 130. In a second stage, the groove in dial 420 are disengaged from thread 416, and linear movement of dial 420 results in retraction of outer tube 130. As shown in FIGS. 12 and 13, the two stages of movement of dial 420 cannot be used simultaneously, and the second stage of movement of dial 420 cannot be used until the first stage of movement of dial 420 has been used to retract outer tube 130 the maximum distance that the first stage can retract outer tube 130.

Figure 14:
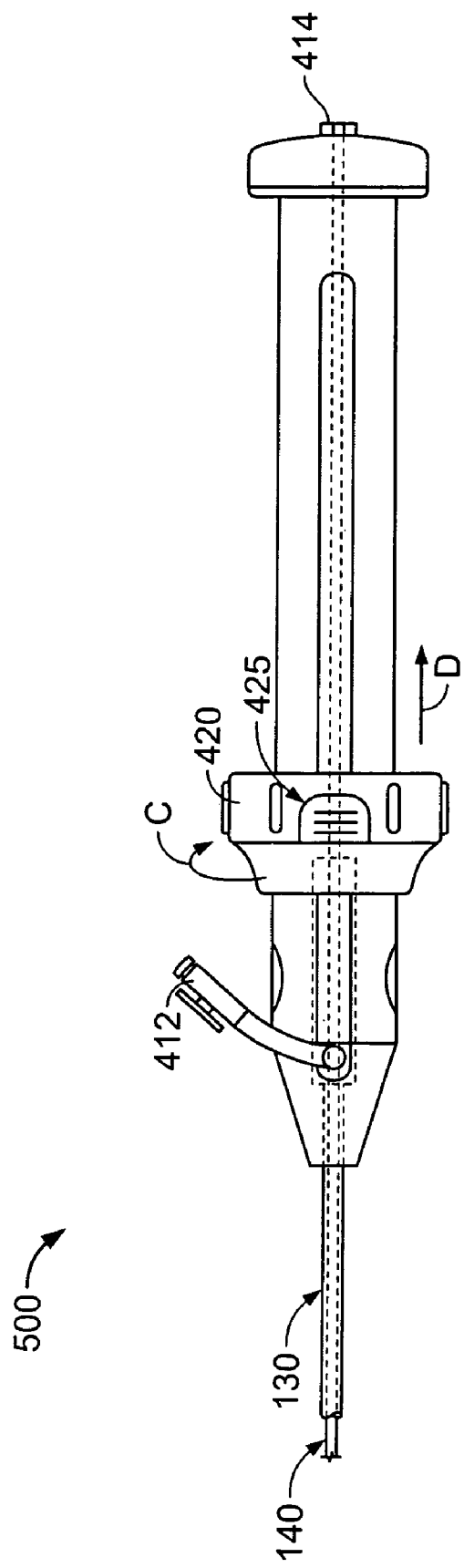
FIG. 14 is a top view of the proximal portion of an embodiment of a stent delivery system.

While systems have been shown as having one actuator with a second stage of movement that cannot be used until a first stage of movement is completed in order to achieve non-continuous change in mechanical advantage, in certain embodiments, one actuator can be used that has two stages in which the actuator does not retract the outer tube the maximum distance that the actuator can in the first stage before the second stage can be used. For example, FIGS. 14 shows the proximal portion a system 500 that is similar to system 400 except that dial 420 includes a release device 425 that disengages the groove in dial 420 from projecting element 416 in handle 410. Device 425 can be any device capable of causing the retraction of element 416 from the groove in dial 420 upon depression of device 425. For example, designed to form a lever with projecting element 416 so that, as device 425 is depressed, projecting element 416 retracts from the groove in dial 420. During use, release device 425 can be activated at any desired time so that the user can switch from the first stage of movement of dial 420 (rotational movement of dial 420 causes retraction of outer tube 130) to the second stage of movement of dial 420 (linear movement of dial 420 causes retraction of outer tube 130) before the first stage of movement of dial 420 has been used to retract outer tube 130 the maximum distance that the first stage can retract outer tube 130.

Figure 15:
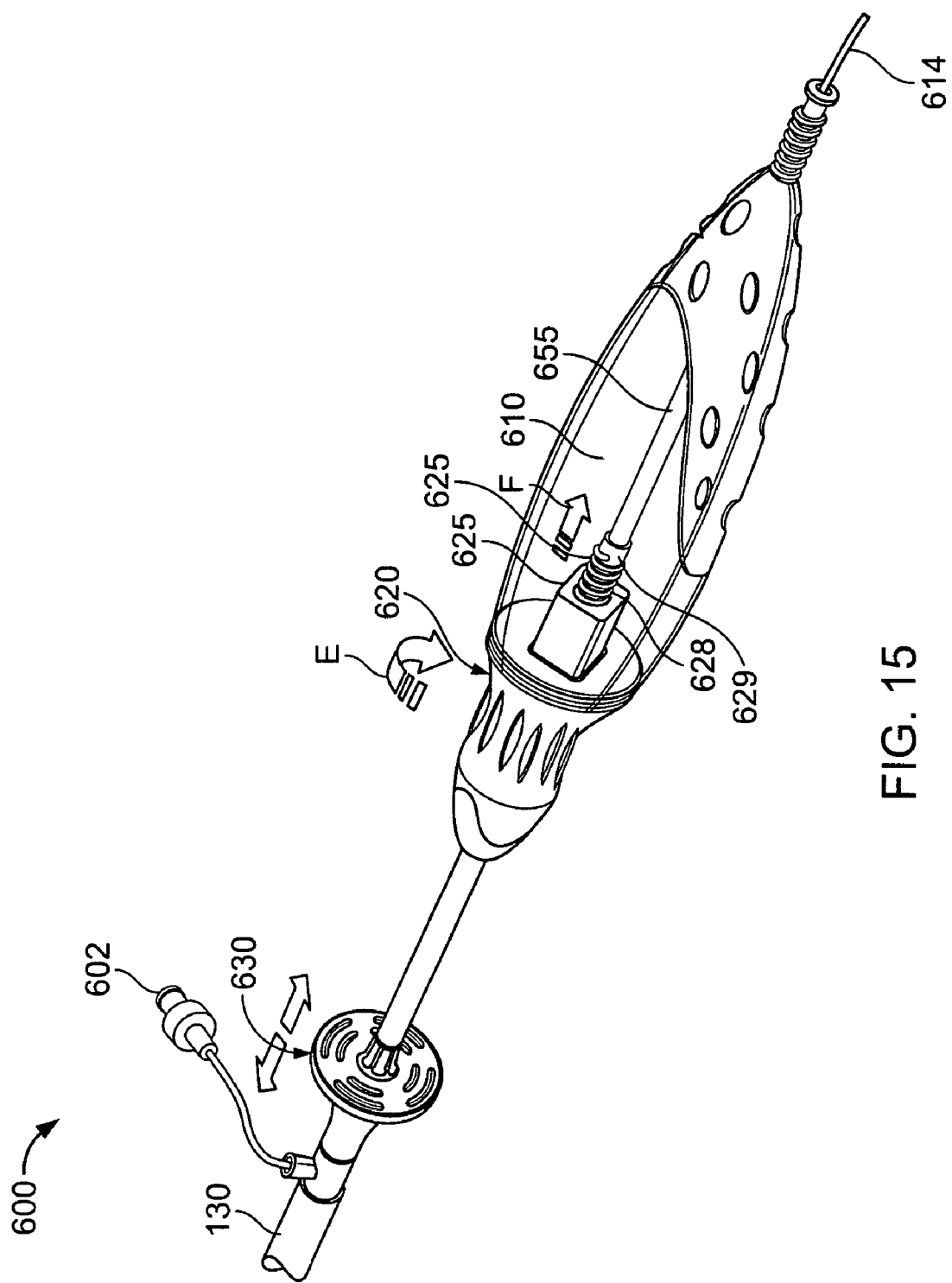
FIG. 15 is a partial cross-sectional view of the proximal portion of an embodiment of a stent delivery system.
Figure 16A:
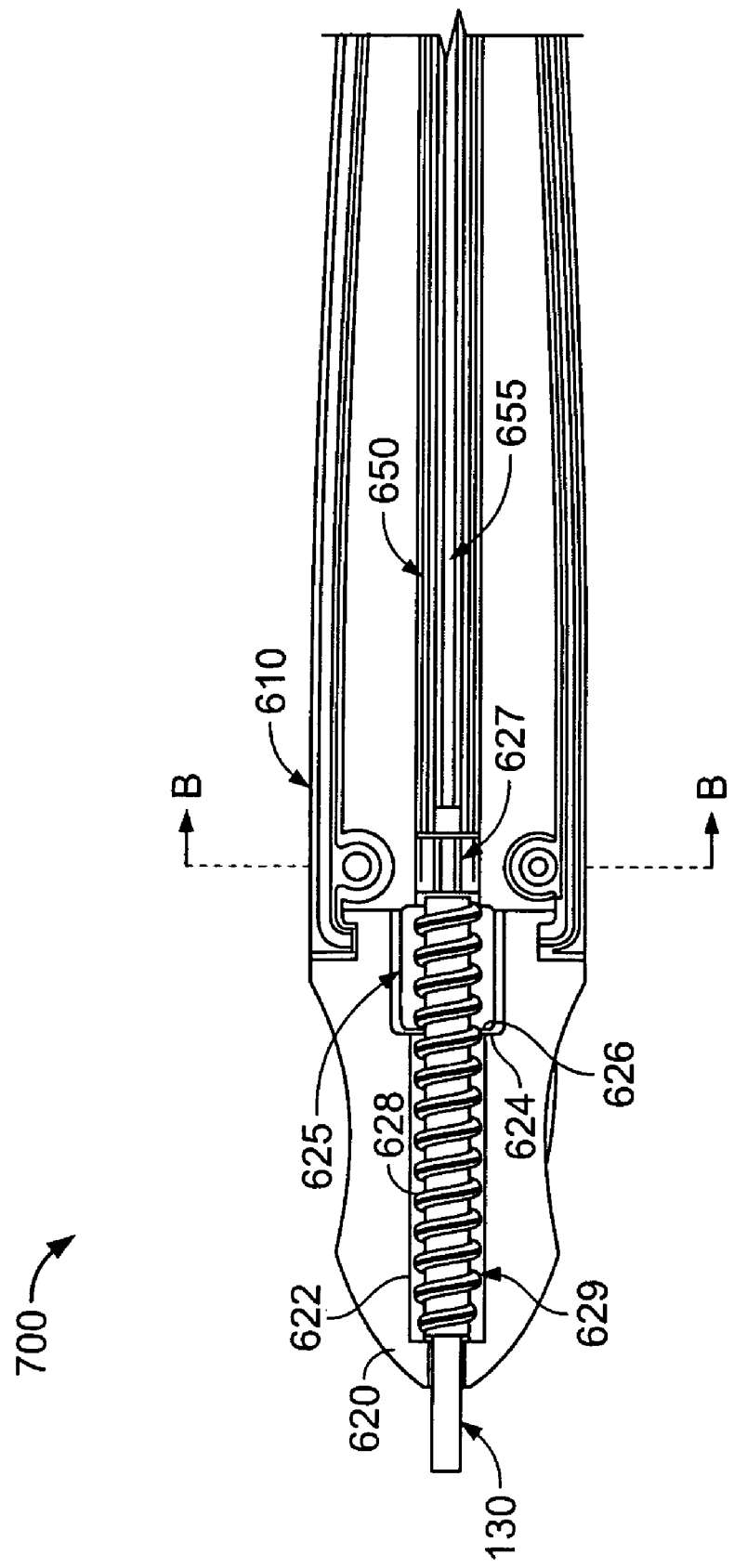
FIG. 16A is a partial cross-sectional view of a portion of the proximal portion of the stent delivery system of FIG. 15.
Figure 16B:
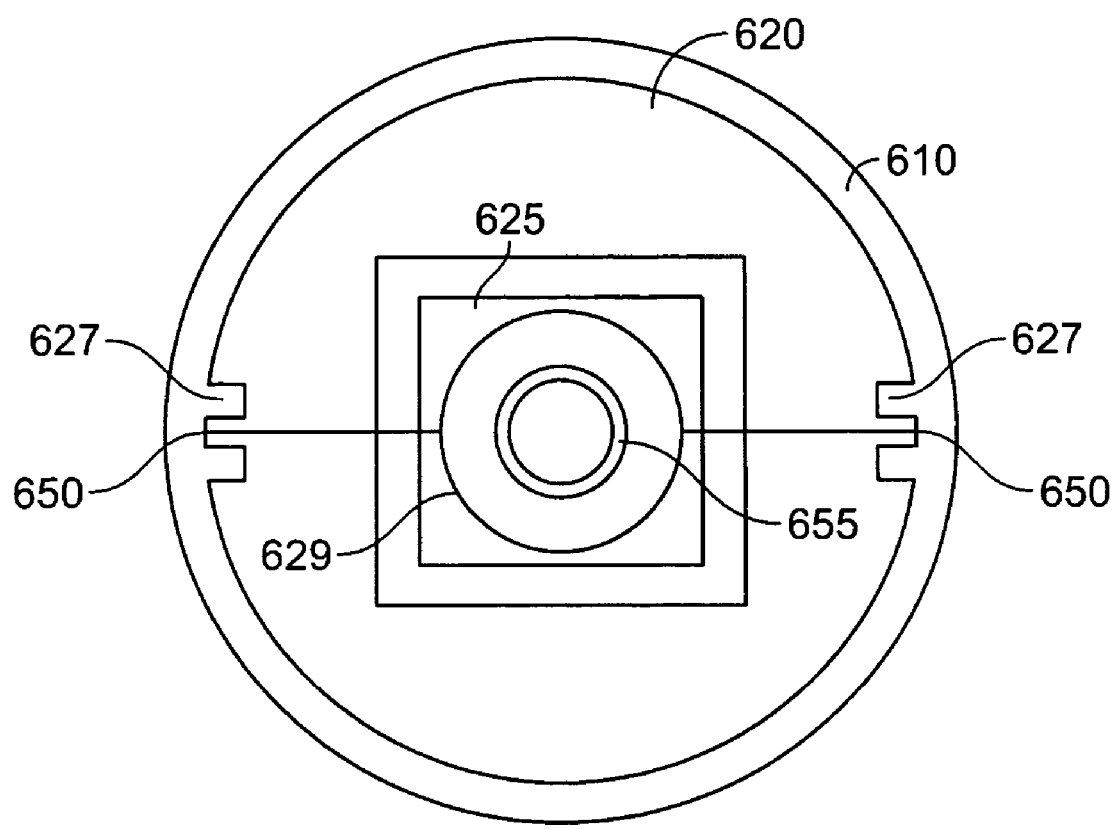
FIG. 16B is a cross-sectional view along line B-B of FIG. 16A.

While systems have been shown in which a single actuator is used to achieve non-continuous change in mechanical advantage as the outer tube is retracted, in some embodiments, more than one actuator can be used to achieve non-continuous change in mechanical advantage as the outer tube is retracted. For example, FIGS. 15, 16A and 16B show the proximal portion of a system 600 having a fluid flush port 602 and a handle 610 that includes a guide wire port 614. System 600 also includes a dial 620, a slidable block 625, a track 650, an inner member (e.g., hypotube) 655, and a graspable member 630. Dial 620 has an open region 622 with a diameter greater than a diameter of a thread 628 on a screw 629. Dial 620 is uncoupled to outer tube 130, but screw 629 is coupled to outer tube 130 so that, when shoulder 624 of dial 620 is in contact with shoulder 626 of block 625, rotating dial 620 (Arrow E) causes outer tube 130 to move proximally. Screw 629 includes wings 627 that fit in track 650 to prevent rotation of outer tube 130 as screw 629 rotates. However, block 625 is dimensioned to fit within both dial 620 and handle 610 so that, at any desired time, graspable member 630 (which is coupled to outer tube 130) can be moved proximally to move outer tube 130 proximally. Thus, system 600 has first and second actuators, each capable of providing a different mechanical advantage, with the second actuator (member 630) being capable of being used before the first actuator (dial 620) moves outer tube 130 the maximum distance that the first actuator can move outer tube 130.

Figure 17:
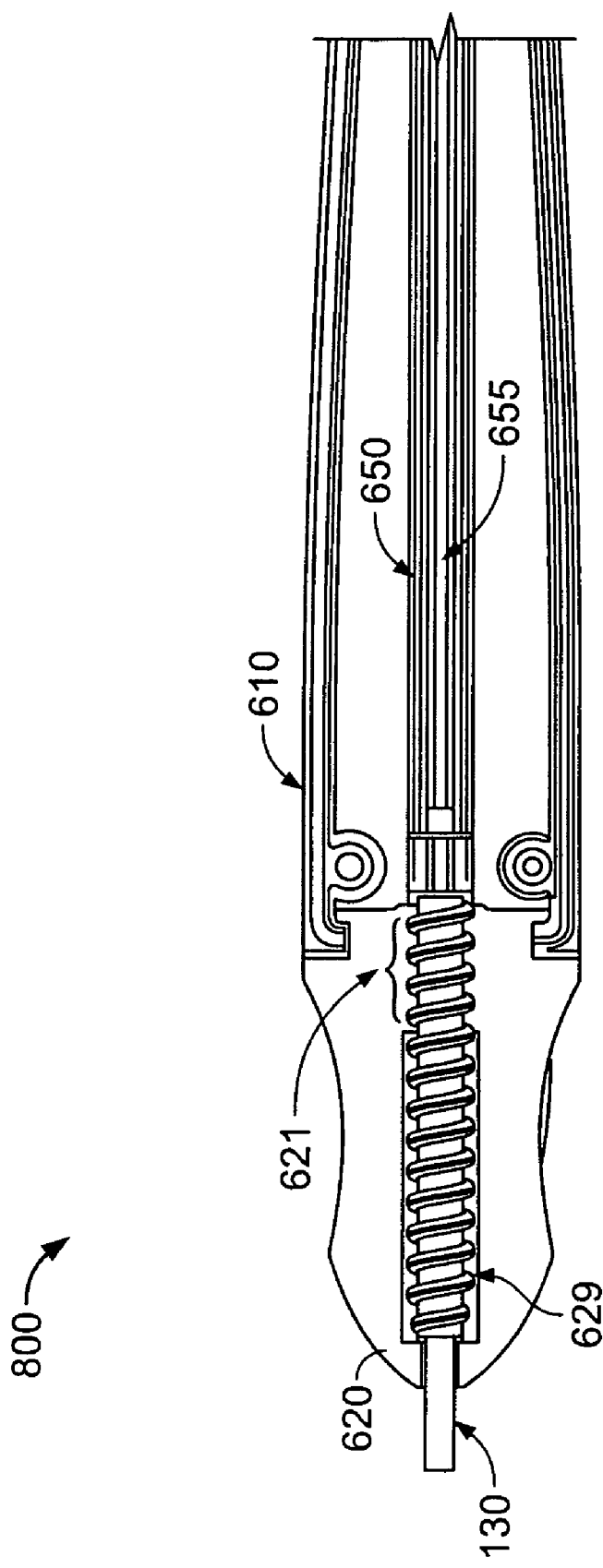
FIG. 17 is a partial cross-sectional view of a portion of the proximal portion of an embodiment of a stent delivery system.

FIG. 17 is a partial cross-sectional view of the proximal portion of a stent delivery system 800 which is similar to system 700, except that system 800 does not include block 625. Instead, dial 620 has a portion 621 with a groove that mates thread 628 of screw 629. With this system, member 630 cannot be used to move outer tube 130 until dial 620 is used to move outer tube 130 the maximum distance that dial 620 can move outer tube 130.

While certain embodiments, have been described, other embodiments are possible.

As an example, while systems have been described which include one or more actuators to retract the outer tube of a stent delivery system, in some embodiments, one or more actuators can be designed to move the outer tube in the distal direction (e.g., by moving a cam in the opposite direction, by moving a shaft in the opposite direction, by rotating a dial in the opposite direction, by rotating a knob in the opposite direction).

As another example, while systems have been described in which the mechanical advantage of the actuator(s) decreases as the actuator(s) move and the outer tube moves, in some embodiments, the mechanical advantage of the actuator(s) can increase as the actuator(s) move and the outer tube moves (e.g., by using a cam with a periphery that decreases as the cam is rotated, by using a shaft with threads having a pitch that increases as the shaft is rotated).

As another example, in some embodiments, a system can include a lock to prevent the actuator(s) from moving.

As an additional example, while stent delivery systems have been described, in certain embodiments, the systems can be used to deliver other medical devices. Such medical devices include, for example, filters (e.g., arterial or venus filters) and stent grafts.

As a further example, while stent delivery systems have been described in which the outer tube is moved proximally by one or more actuators, more generally the actuator(s) can be used to cause relative motion between the inner and outer tubes. As an example, in some embodiments, the actuator(s) can cause the inner tube to move (e.g., move distally) with or without causing the outer tube to move.

Other embodiments are in the claims.

The invention claimed is:
1. A system, comprising:
an inner tube;
an outer tube at least partially surrounding the inner tube so that a medical device can be positioned between the inner and outer tubes, the inner and outer tubes being configured to be capable of being disposed within a body lumen; and
an actuator configured so that, as a force is applied to the actuator, the actuator can cause relative motion between the inner and outer tubes,
wherein the actuator comprises a rotatable member having a first portion with a radius that gradually increases around a circumference of the rotatable member and a second portion with a stepwise change in radius, radius being determined relative to an axis of rotation of the rotatable member, wherein a mechanical advantage of the actuator changes as the actuator moves in a proximal direction, wherein a rotatable element is coupled to the rotatable member so that, as the rotatable element rotates, the rotatable member rotates, wherein the rotatable element is an external thumb wheel; and wherein the mechanical advantage of the actuator linearly decreases as the actuator moves in the proximal direction so that the actuator provides fine and controlled proximal refraction of outer tube when the thumb wheel is initially rotated and coarse proximal retraction of outer tube when the thumb wheel is later rotated.

2. The system of claim 1, further comprising a housing coupled to the actuator.

3. The system of claim 2, wherein the actuator is at least partially disposed within the housing.

4. The system of claim 2, wherein at least a portion of the housing is proximal to a proximal end of the outer tube.

5. The system of claim 2, wherein the housing is configured to be held by an operator of the system during use of the system.

6. The system of claim 1, wherein the actuator comprises a cam.

7. The system of claim 1, further comprising a windable member that couples the rotatable member to the outer tube.

8. The system of claim 7, wherein the windable member is selected from the group consisting of wires, cords, ribbons, flat gears and combinations thereof.

9. The system of claim 7, wherein the windable member comprises a wire.

10. The system of claim 1, wherein the rotatable member is integral with the rotatable element.

11. The system of claim 1, wherein the rotatable element is configured to be rotated by an operator of the system during use of the system.

12. The system of claim 1, wherein the rotatable element is positioned proximal to a proximal end of the outer tube.

* * * * *

UNITED STATES PATENT AND TRADEMARK OFFICE
CERTIFICATE OF CORRECTION

| | | |
|---|---|---|
| PATENT NO. | : 7,967,829 B2 | Page 1 of 1 |
| APPLICATION NO. | : 10/874336 | |
| DATED | : June 28, 2011 | |
| INVENTOR(S) | : Richard C. Gunderson et al. | |

It is certified that error appears in the above-identified patent and that said Letters Patent is hereby corrected as shown below:

Column 9
Line 11, delete "refraction", and insert therefor -- retraction --.

Signed and Sealed this
Sixteenth Day of August, 2011

David J. Kappos
*Director of the United States Patent and Trademark Office*